US00PP35030P3

(12) United States Plant Patent
Ruter

(10) Patent No.: US PP35,030 P3
(45) Date of Patent: Mar. 14, 2023

(54) ***THUJA* PLANT NAMED 'RUTTHU2'**

(50) Latin Name: ***Thuja* species**
Varietal Denomination: RutThu2

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/854,183

(22) Filed: Jun. 30, 2022

(65) Prior Publication Data

US 2023/0007820 P1 Jan. 5, 2023

Related U.S. Application Data

(60) Provisional application No. 63/217,004, filed on Jun. 30, 2021.

(51) Int. Cl.
*A01H 7/00* (2006.01)

(52) U.S. Cl.
USPC ..... Plt./213
CPC ..... *A01H 7/00* (2013.01)

(58) Field of Classification Search
USPC ..... Plt./213
CPC ..... A01H 7/00
See application file for complete search history.

*Primary Examiner* — Anne Marie Grunberg
(74) *Attorney, Agent, or Firm* — Thomas Horstemeyer, LLP

(57) ABSTRACT

A new and distinct cultivar of *Thuja* plant named 'RutThu2', characterized by its compact, mounding, spreading form with unusual, thread-leaf shoots; growth in USDA Zone 8a, growth in full sun and part-shade conditions in landscape and container production, and better heat tolerance than other thread-leaf forms of *Thuja occidentalis* or *Thuja plicata* 'Whipcord'.

2 Drawing Sheets

Figure 1:
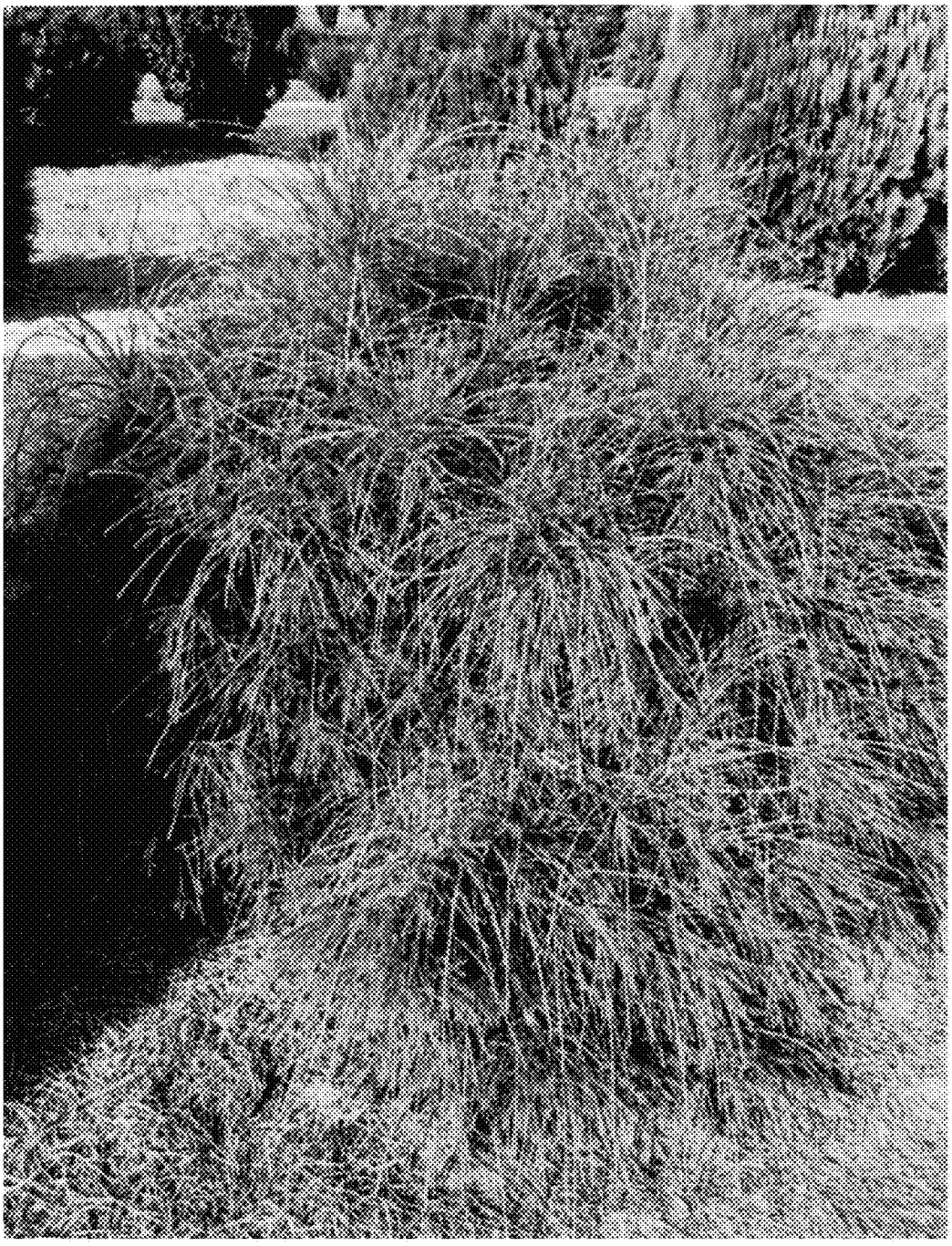

Botanical designation: *Thuja* species.
Cultivar denomination 'RutThu2'.

BACKGROUND OF THE INVENTION

The present invention relates to a new and distinct cultivar of *Thuja*, botanically know as *Thuja occidentalis*, and hereinafter referred to by the cultivar name 'RutThu2'.

The new *Thuja* cultivar 'RutThu2' is a product of open pollination of *Thuja occidentalis* 'Filiformis' (unpatented). The open-pollinated seeds were obtained in 2010 (third accession). Seedlings were planted in Watkinsville in 2015. The new cultivar 'RutThu2' was selected for its compact, mounding form, unusual, thread-leaf shoots, heat tolerance, and growth in full-sun to partial shade.

Asexual reproduction of the new *Thuja* 'RutThu2' using hardwood cuttings has been continued in Watkinsville, Ga. since 2015. Observations of the resulting progeny have shown that the unique features of this new *Thuja* 'RutThu2' are stable and reproduced true to type in successive generations. The new 'RutThu2' has also been grown in MN.

SUMMARY OF THE INVENTION

The new *Thuja* cultivar 'RutThu2' has not been observed under all possible environmental conditions. The phenotypes may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Thuja* cultivar named 'RutThu2'. In combination, these traits set 'RutThu2' apart from all other existing varieties of *Thuja* known to the inventors.

1. attractive mounding, spreading form with unusual, thread-leaf shoots similar to *Thuja occidentalis* 'Filiformis' (unpatetend) and 'Nuclear Blast' (unpatetend);
2. grows and thrives in USDA zone 8a (as compared to *Thuja occidentalis* 'Filiformis' and 'Nuclear Blast', USDA zone 7 plants that have not survived in Zone 8a);
3. growth in full sun or part-shade in the landscape;
4. growth in full sun or up to 55% shade in container production;
5. Better heat tolerance than other thread-leaf forms of *Thuja occidentalis* or *Thuja plicata* 'Whipcord' (unpatetend)

Plants of the 'RutThu2' can be compared to similar cultivar *Platycladus orientalis* 'Franky Boy' (unpatetend) and differ from 'Franky Boy' in that 'RutThu2' has a mounding-spreading shape as opposed to oval and is shorter and wider than 'Franky Boy' (which is about 96"×72", as compared to about 40"×84" for 'RutThu2'). Male parent plant is not conclusively known, so comparison data is not available. The new *Thuja* 'RutThu2' can also be compared to thread-leaf *Thuja occidentalis* cultivars 'Filiformis' (female parent) and 'Nuclear Blast' and *Thuja plicata* 'Whipcord'. *Thuja* 'RutThu2' is able to survive and thrive in USDA Zone 8a unlike varieties 'Filiformis' and 'Nuclear Blast', and 'RutThu2' also has better heat tolerance than *Thuja plicata* 'Whipcord'.

BRIEF DESCRIPTION OF THE PHOTOGRAPHS

The accompanying, colored photographic illustrations show the overall appearance and distinct characteristics of the new cultivar *Thuja* 'RutThu2' showing the colors as true as possible. Colors in the photographs may differ slightly from the color values cited in the detailed botanical description. The photographs were taken around June, 2021 of plants grown outdoors in Watkinsville, Ga.

The photograph labeled FIG. 1 depicts a side view of a typical 8-year-old 'RutThu2' plant showing the compact form and features.

Figure 2:
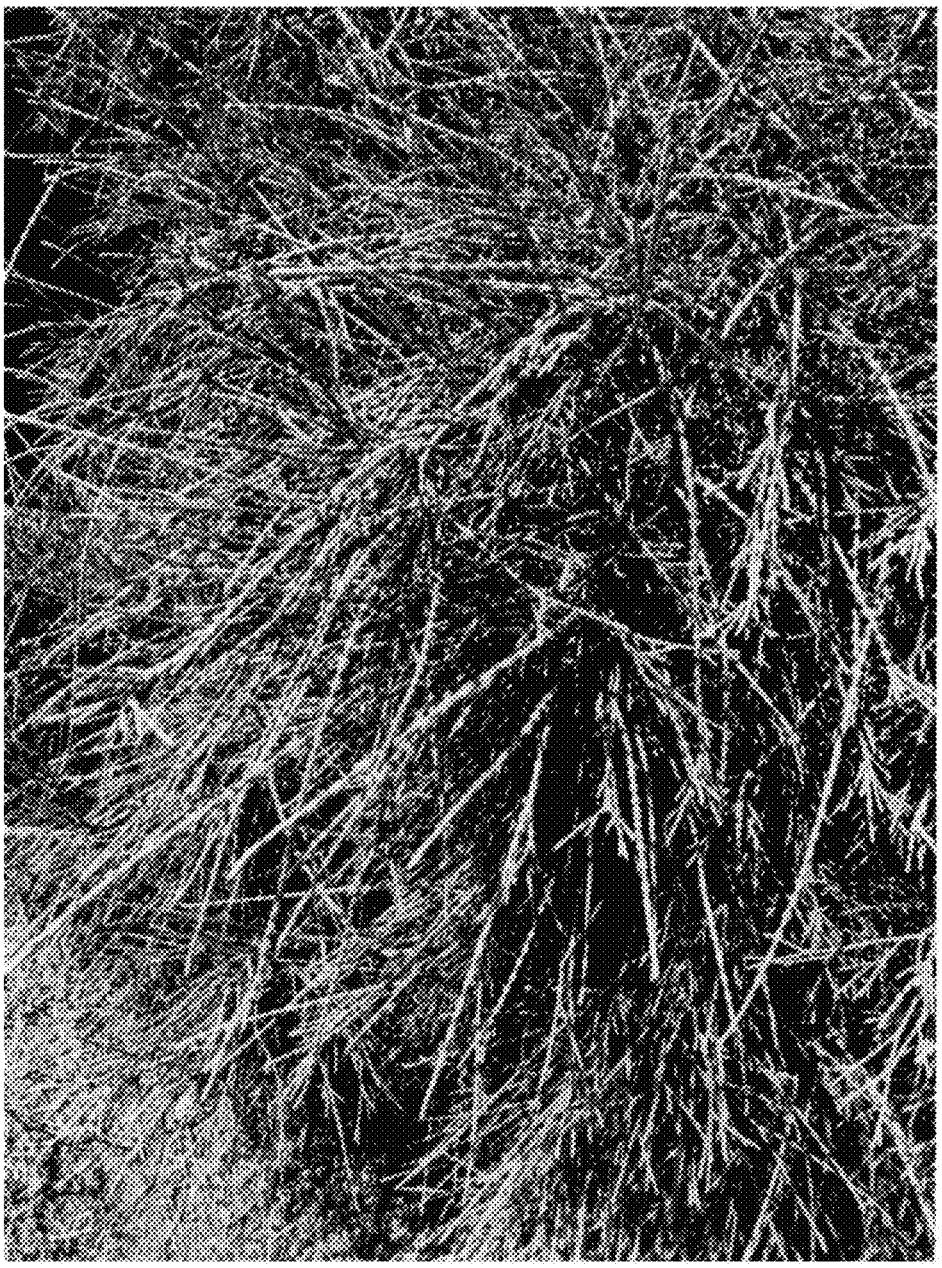

The photograph labeled FIG. 2 depicts a close-up view of the branches and needles of a typical 8-year-old 'RutThu2' plant showing the thread-leaf shoots.

DETAILED BOTANICAL DESCRIPTION

The following traits have been consistently observed in the original plants of the new varieties and in asexually propagated progeny grown in Tifton, Ga., (and some in MN) and, to the best knowledge of the inventors, their combination forms the unique characteristics of the new variety 'RutThu2'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used The aforementioned photographs and following observations, measurements, and values describe plants of the *Thuja* cultivar named 'RutThu2'. Data were collected from a horticulture farm in Watkinsville, Ga. from 6-year-old plants. The average low temperatures ranged from about 20° F. to 30° F. in the winter and about 90° F. to 100° F. in summer.

Botanical classification: *Thuja* 'RutThu2'.

Commercial classification: Ornamental conifer.

Parentage: Open pollination of *Thuja occidentalis* 'Filiformis' by unknown pollen parents.

Growth and propagation:

*Propagation type.*—Terminal or sub-terminal hardwood cuttings.

*Growth rate.*—Slow to moderate.

*Root description.*—Typically about 2-5 roots arising from the base of the cuttings.

*Rooting habit.*—Slow for *Thuja occidentalis.*

Plant description:

*Habit.*—Of 6-year-old plant in field — mounding-spreading.

*Usage.*—Various uses, including landscaping, ornamental, container, border, hedge, and mass planting.

*Vigor.*—Slow to moderate.

*Size of 6-year-old plant.*—A. Height: from soil level to top of plant, about 40 inches. B. Width: about 80-84 inches. C. Ratio: about 0.48.

*Branch/stem (terminal tuft).*—A. Quantity: numerous. B. Length: about 5-15 cm. C. Base Diameter: about 3-4 mm at 15 cm from tip. D. Branch angle: about 15°±5 from center. E: Odor (of bruised stem): pleasant evergreen. F. Internode length: about 1-3 mm (about 5 internodes per sample). G: Color (RHS): Greyed-orange 167A. H: Strength of lateral branches: well-attached but weeping. I: Pubescence: none. J: Shape: round.

*Leaf.*—A. Leaf type: scale. B. Mature size (L×W): about 4-5 mm×about 1.5-2.0 mm. C. Arrangement on stem: decussate. D. Aspect: appressed. E. Color (RHS): summer — adaxial, Green 143C; abaxial, Green 144A. winter — Greyed-orange 165A. F. Leaf Number: average of about 6 per cm/stem. G. Apex: attenuate. H. Base: rounded. I. Margin: Hyaline-entire. J. Shape: scale; lobes absent. K. Pubescence: none. L. Venation: none. M. Texture: waxy with abaxial gland. O. Odor when crushed: pleasant evergreen.

*Long shoots.*—A. Facial Gland: present. B. Leaf Shape: scale. C. Color: Grey Brown 199D. D. Tips: free. E. Apex: acuminate/cuspidate.

*Coning production.*—None.

*Seed.*—None.

Weather/temperature tolerance: Plants of the new *Thuja* have been observed to grow in USDA Zone 8a, with better heat tolerance than similar *Thuja* cultivars, and have a USDA Zone range 3-8. 'RutThu2' thrives in full sun and part-shade in landscape and container production.

Disease/pest resistance: To date, plants of the new *Thuja* have been observed to have similar disease/pest resistance as other *Thuja* cultivars grown under similar conditions.

It is claimed:

1. A new and distinct cultivar of the *Thuja* plant named 'RutThu2' as illustrated and described herein.

* * * * *